United States Patent
Adachi et al.

(10) Patent No.: US 6,395,347 B1
(45) Date of Patent: May 28, 2002

(54) MICROMACHINING METHOD FOR WORKPIECE OBSERVATION

(75) Inventors: Tatsuya Adachi; Takashi Kaito; Yoshihiro Koyama; Kouji Iwasaki, all of Chiba (JP)

(73) Assignee: Seiko Instruments Inc., Chiba (JP)

( * ) Notice: Subject to any disclaimer, the term of this patent is extended or adjusted under 35 U.S.C. 154(b) by 0 days.

(21) Appl. No.: 08/351,093

(22) Filed: Nov. 30, 1994

(30) Foreign Application Priority Data

Nov. 30, 1993 (JP) .............................. 5-300322

(51) Int. Cl.$^7$ .................................. H01J 3/00
(52) U.S. Cl. ...................... 427/526; 427/562; 427/582; 216/2; 216/11; 250/311; 250/492.21; 438/706; 438/712; 438/725
(58) Field of Search .............................. 427/525, 526, 427/531, 562, 564, 582, 584; 156/626.1, 643.1, 646.1, 654.1, 659.4, 662.1; 216/2, 11; 250/492.21, 311, 307, 310; 438/706, 712, 725

(56) References Cited

U.S. PATENT DOCUMENTS

| | | | | |
|---|---|---|---|---|
| 4,612,085 A | * | 9/1986 | Jelks et al. | 427/584 |
| 4,698,236 A | * | 10/1987 | Kellogg et al. | 430/5 |
| 4,874,632 A | * | 10/1989 | Nakagawa et al. | 427/526 |
| 4,876,112 A | * | 10/1989 | Kaito et al. | 427/526 |
| 4,902,530 A | * | 2/1990 | Yasuka et al. | 427/526 |
| 5,104,684 A | * | 4/1992 | Tao et al. | 427/526 |
| 5,145,554 A | * | 9/1992 | Seki et al. | 156/646.1 |
| 5,378,316 A | * | 1/1995 | Franke et al. | 156/646.1 |
| 5,525,806 A | * | 6/1996 | Iwasaki et al. | 205/307 |

FOREIGN PATENT DOCUMENTS

| | | | | |
|---|---|---|---|---|
| EP | 0153854 | * | 9/1985 | 427/526 |
| JP | 02-145770 | * | 6/1990 | 427/526 |
| JP | 04-337445 | * | 11/1992 | |
| JP | 05-34250 | * | 2/1993 | |
| JP | 05-136097 | * | 6/1993 | |
| JP | 06-180277 | * | 6/1994 | |

* cited by examiner

Primary Examiner—Martin Angebranndt
(74) Attorney, Agent, or Firm—Hogan & Hartson, L.L.P.

(57) ABSTRACT

A method for preparing a sample for observation, by the steps of: contacting a first predetermined area of the sample surface with an organic compound vapor while irradiating the first predetermined area with an ion beam to decompose the organic compound into a layer having a mask function, the layer covering the first predetermined area; and contacting a second predetermined area of the sample surface with an etching gas while irradiating the second predetermined area with an ion beam in order to remove material from the sample surface at the second predetermined area, wherein the second predetermined area includes at least part of the first predetermined area and the layer covering the first predetermined area prevents removal of material from the sample surface in the first predetermined area.

14 Claims, 2 Drawing Sheets

MICROMACHINING METHOD FOR WORKPIECE OBSERVATION

BACKGROUND OF THE INVENTION

The present invention relates to micromachining a sample, for example of semiconductor material, for observation of the sample by detection of electron or ion beam radiation transmitted through, or penetrating, the sample. Such observations are generally performed with a transmission electron microscope (TEM).

When a sample is observed by using TEM in the prior art, a region of the sample which is to be observed is processed to have a thickness in the submicron range, an electron beam is transmitted via a lens through the sample and a magnified image of the sample is formed on a photographic plate through a lens from the transmitted electron beam. In order for the electron beam to be transmitted through the sample, the sample must be made very thin. Production of a thin sample according to the prior art for the observation of the sample using the transmission electron microscope is very time consuming and labor intensive.

When a predetermined cross section of a semiconductor integrated circuit is observed by prior art techniques, a sample is mechanically machined to a thickness of more or less several tens of microns with a predetermined point which is to be observed located at a center region, and then the sample is etched by a wet or dry process from one or two sides adjacent the center region to a predetermined thickness for TEM observation.

But it is difficult in the prior art to obtain a thickness of 0.1–0.5 $\mu$m of a sample for TEM observation, including the predetermined point, through etching by a wet or dry process. Especially it was difficult to keep the predetermined point for observation left on the sample as it is.

SUMMARY OF THE INVENTION

It is an object of the present invention to improve the preparation of a sample for observations of the above described type.

It is a particular object of the invention to prepare a sample for such observation while eliminating the shortcomings of prior art methods.

The above and other objects are achieved, according to the present invention, by a method for preparing a sample for observation, the sample having a surface, the method comprising:

contacting a first predetermined area of the sample surface with an organic compound vapor while irradiating the first predetermined area with an ion beam to decompose the organic compound into a layer having a mask function, the layer covering the first predetermined area; and contacting a second predetermined area of the sample surface with an etching gas while irradiating the second predetermined area with an ion beam in order to remove material from the sample surface at the second predetermined area, wherein the second predetermined area includes at least part of the first predetermined area and the layer covering the first predetermined area prevents removal of material from the sample surface in the first predetermined area.

According to preferred embodiments of the invention:
the same ion beam is used in both contacting steps;
the ion beam is focussed;
each irradiating step comprises scanning the respective predetermined area with the focussed ion beam; and
each contacting step comprises spraying a respective gas at the respective predetermined area from a respective small diameter nozzle.

When the focussed ion beam repeatedly scans and irradiates a first predetermined area which is rectangular on a sample surface, while an organic compound vapor is sprayed through a small diameter spraying nozzle on that area, the organic compound absorbed on the sample surface at the first predetermined area is decomposed by the irradiation of the focussed ion beam. Such decomposed organic compound forms a film at the first predetermined area of the sample. The first predetermined area which is rectangular has a shape with a thickness sufficient to be observed by a TEM, with area being properly positioned for the TEM observation.

Next, simultaneously with the irradiation by the ion beam at the second predetermined area, which includes at least a part of the first predetermined area on which the above-mentioned film is formed, the film formed on the first predetermined area functions as a mask against etching and only sample surface areas not covered by the film and irradiated by the ion beam are etched due to the spraying of the etching gas, which magnifies the etching effect of the ion beam. Thus a thick sample cross section is obtained for TEM observation.

DESCRIPTION OF THE PREFERRED EMBODIMENTS

Figure 1:
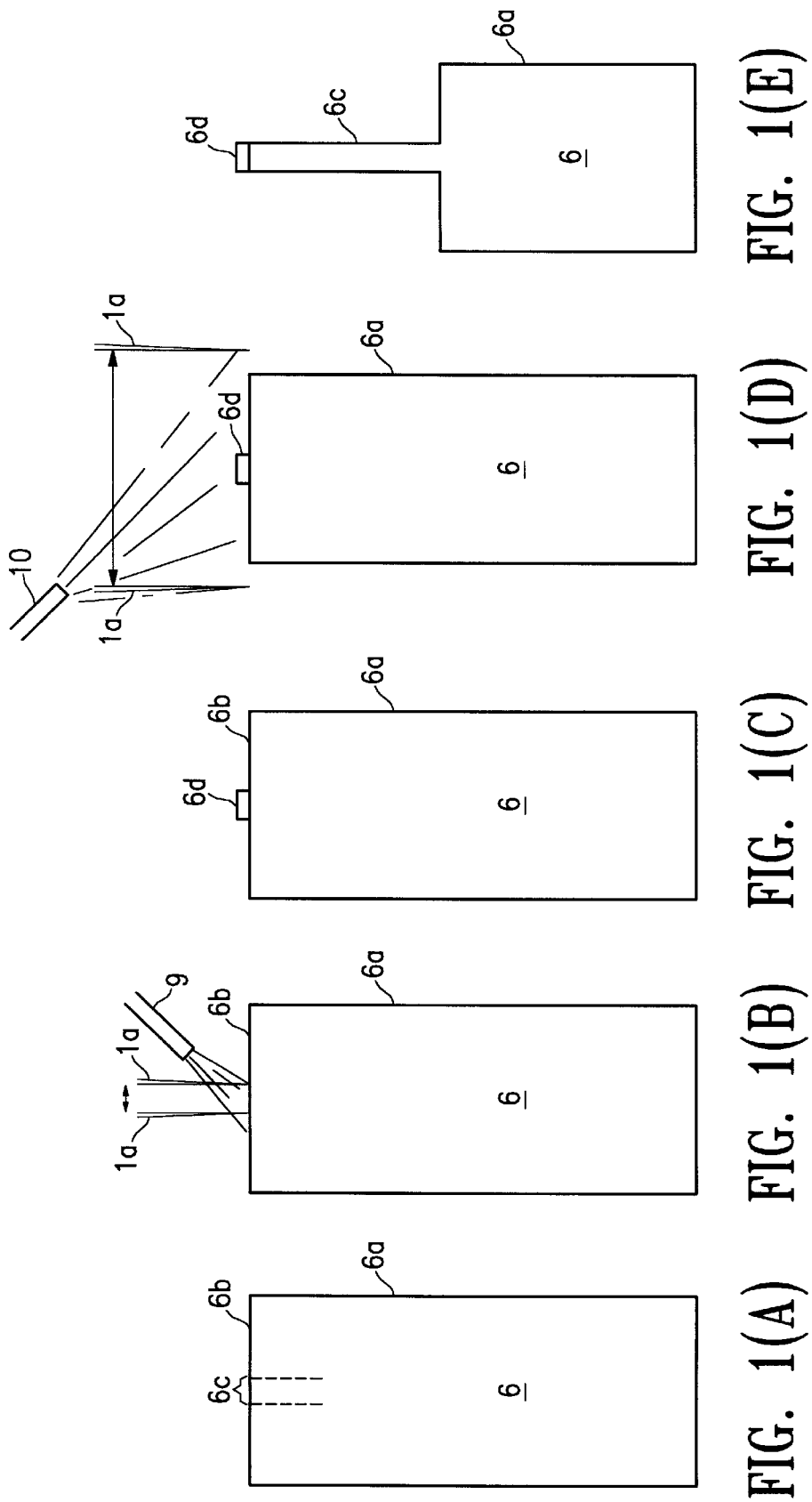
FIGS. 1(A), 1(B), 1(C), 1(D) and 1(E) are elevational pictorial views illustrating various stages in the performance of an embodiment of the method according to the present invention.

A preferred embodiment of the invention will be described with reference to the drawing.

Figure 2:
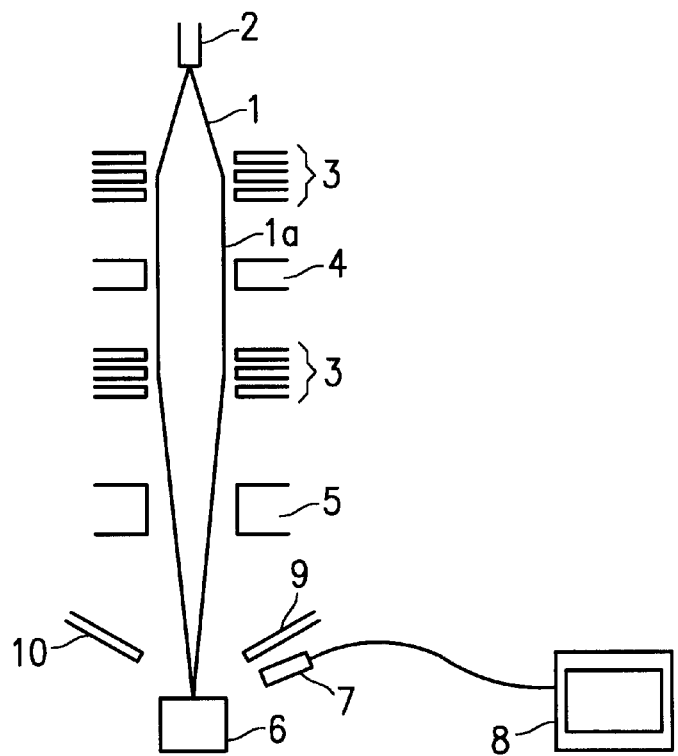
FIG. 2 is a cross-sectional view showing a focussed ion beam in processing equipment for carrying out the micromachining method of the present invention.

FIG. 2 shows a cross section of a focussed ion beam processing equipment which is used for the embodiment of the invention. A gallium liquid metal ion beam 1 is generated from a liquid metal ion source 2. Beam 1 is formed into a focussed ion beam 1a by a first part of an electrostatic lens 3. Passing through the electrostatic lens 3, focussed ion beam 1a passes a beam blanker 4 for selectively blocking beam 1a or allowing beam 1a to irradiate a sample 6. Focussed ion beam 1a which passed beam blanker 4 is focussed further by a second part of electrostatic lens 3. Focussed ion beam 1a which passes the second part of electrostatic lens 3 is deflected and scanned by scanning electrode 5, and irradiates a surface 6b (see FIGS. 1(A)–1(C) and 3) of sample 6.

Setting of the irradiation area of focussed ion beam 1a on surface 6b of sample 6 is effected by controlling the deflection of focussed ion beam 1a by scanning electrode 5, as well as by beam blanker 4. Secondary charged particles generated from surface 6b of sample 6 in response to irradiation by focussed ion beam 1 is detected by a secondary charged particle detector 7 and an image of surface 6b of sample 6 is displayed on an image display 8 based on the detection by secondary charged particle detector 7.

A spraying nozzle 9 for spraying an organic compound is disposed for spraying a vapor of the organic compound towards the irradiation point of focussed ion beam 1a on surface 6b of sample 6. Nozzle 9 has a very small inside diameter in order to blast organic compound vapor onto a small spot on surface 6b of sample 6, and nozzle 9 is connected to an on/off valve (not shown) for controlling the delivery of the organic compound vapor to nozzle 9.

Moreover, an etching gas spraying nozzle 10 is disposed for blasting an etching gas onto the irradiation point of focussed ion beam 1a on surface 6b of sample 6. Etching gas spraying nozzle 10 also has a very small inside diameter in order to blast etching gas vapor onto a small spot on surface 6b of sample 6 and it has also an on/off valve (not shown) for controlling the delivery of the etching gas to nozzle 10.

Next, with reference to FIGS. 1(A)–1(E), TEM observation of sample 6 which has a cross section of a semiconductor integrated circuit will be described. FIGS. 1(A)–1(E) are pictorial elevational, cross-sectional views showing various stages in a micromachining procedure according to the invention.

First, a sample 6 having a width of more or less 20 μm is cut off, e.g. from a wafer, with a dicing saw and with the aid of a microscope such that an observation point of the sample is as close the center of the sample as possible.

FIG. 1(A) shows such a sample 6 which has been cut with the dicing saw. The width of the circuit side surface 6b between two cross-sectional surfaces 6a cut with the dicing saw is about 20 μm, although the width does not necessarily have precisely this value. By controlling scanning electrode 5 and/or beam blanker 4, repetitive scanning and irradiating of focussed ion beam 1a on surface 6b of sample 6 is performed in a region which includes at least a part of a first predetermined area included in the scanning area associated with etching, this scanning area being referred to herein as a "second predetermined area".

As shown in FIG. 1(D), simultaneously with this irradiation above, xenon fluoride gas is blasted onto the second predetermined area from etching gas blasting nozzle 10 to etch sample surface 6b. The ion beam increases the etching effect of the xenon fluoride gas on silicon and silicon dioxide, which are exemplary materials of sample 6. But since it has almost no etching effect on a carbon film 6d which was previously deposited on surface 6b, carbon film 6d performs a kind of mask function in ion beam assisted etching with xenon fluoride gas.

Sample 6 set in an irradiation position of focussed ion beam 1a generated by the focussed ion beam processing equipment described above.

Focussed ion beam 1a is scanned across, and irradiates, surface 6b of sample 6, and secondary charged particles generated and emitted from surface 6b due to the irradiation described above are detected by means of secondary charged particle detector 7, and an image of sample surface 6b is displayed on image display 8.

Next, as shown in FIG. 1(B), the first predetermined area, which is a rectangular shaped part of the scanning area of focussed ion beam 1a, is repeatedly scanned and irradiated, controlled by scanning electrode 5 and/or beam blanker 4 in a way that surface 6b is at the TEM observation position.

Simultaneously with irradiation, pyrene vapor of hydrocarbon gas as the organic compound vapor is projected from organic compound spraying nozzle 9.

The scanning area of focussed ion beam 1a in this process is the first predetermined area. Pyrene deposited on surface 6b of sample 6 is converted to a film of carbon through decomposition due to irradiation by focussed ion beam 1a. Through repetition of this scanning while pyrene continues to be projected, a comparatively thicker carbon film 6d can be formed as shown in FIG. 1(C). When carbon film 6d has the desired thickness, flow of organic compound vapor from spraying nozzle 9 is halted.

Then, by delivery of etching gas from nozzle 10 and ion beam irradiation of the second predetermined area, sample 6 is etched to leave an isolated portion 6c whose top surface constitutes the first predetermined area, as shown in FIG. 1(E). This result is achieved by repetitive scanning of focussed ion beam 1a onto the second predetermined area. Portion 6c is then ready for TEM observation.

Figure 3:
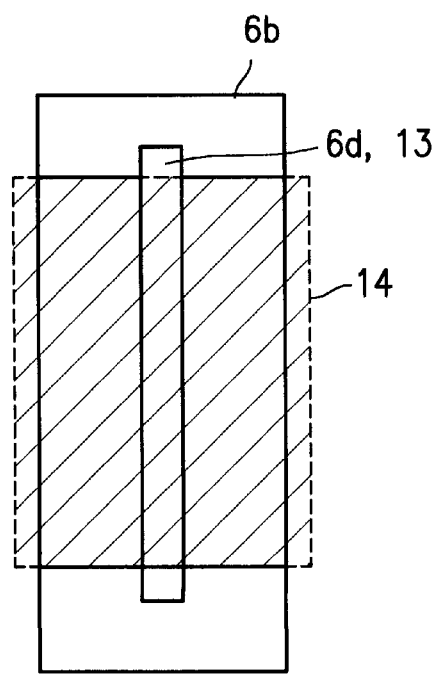
FIG. 3 is a detail plan view of a sample processed by the method according to the present invention.

FIG. 3 is a plan view of a sample 6 which is prepared according to the invention. In the plane of FIG. 3, sample 6 has a rectangular shape. On the portion of surface 6b of sample 6 to be observed by TEM, carbon film 6d is formed. Film 6d covers the first predetermined area, which is the scanning area of the focussed ion beam during carbon film deposition. The width of the first predetermined area is selected to be suitable for TEM observation around the center of circuit side surface 6b.

In FIG. 3, the crosshatched area 14 is the second predetermined area, which is the focussed ion beam scanning area during etching. This second predetermined area includes at least a part of first predetermined area, which may be the whole area over sample surface 6b in FIG. 3. Since the part 6c to be left after etching is very thin, and is thus fragile, it would be advantageous to leave material of sample 6 along each vertical edge of part 6c. In other words, if the scanning ion beam only covers area 14 during etching, portions of sample 6 will be left at the top and bottom of FIG. 3. These portions support the edges of part 6c and thus give part 6c additional strength. This result can also be achieved by depositing film 6d beforehand on the parts of surface 6b which are not to be etched.

The part or parts of the second predetermined area on sample surface 6b where material is to be removed, i.e. which are not part of the first predetermined area, are etched and eliminated through ion beam assisted etching, as described above. During this procedure, carbon film 6d formed on the first predetermined area becomes a mask preventing ion beam assisted etching. That is, a region corresponding to a thick surface layer of sample 6, which region is part 6c, is formed for TEM observation.

In the embodiment described above, the same conditions of electric current, voltage, beam spot diameter, etc. are used for observation of surface 6b of sample 6, for forming film 6d, which acts as a mask, on sample surface 6b and for ion beam assisted etching of part of sample 6. But the degree of precision needed for ion beam assisted etching is not as great as that required for other operations forming part of this method. Therefore, current and voltage can be higher and beam spot diameter can be larger in the former in terms of focussed ion beam scanning and irradiating than in the case of the latter, and this leads to better efficiency in etching for elimination.

Moreover, the same objective can also be attained by projecting etching gas simultaneously with irradiation of sample surface 6b without scanning and without fine focussing, by irradiating surface 6b with a wide, collimated beam.

As the organic compound vapor used to form film 6d, not only pyrene gas but also a hydrocarbon gas such as phenanthrene gas or a metal carbonyl vapor such as tungsten carbonyl vapor and molybdenum carbonyl vapor can be used for forming a tungsten or molybdenum metal film as the masking film. Since such metal film has an antietching capability, it can also be used in the practice of the present invention.

As the etching gas, use can also be made of a halogen gas such as chlorine or iodine gas etc. or a halogen compound gas such as carbon tetrachloride gas. Sometimes it is more effective to etch by changing between different kinds of gas according to the kind of materials to be etched, if necessary or with use of a mixed gas such as, for example, choline iodine gas etc. which is highly effective for etching aluminum wiring.

Methods according to the present invention provide improved setting of the observation point on a sample and a substantial increase in the degree of precision of the resulting observations and measurements. In addition, efficiency in processing increases very much since thin film forming for TEM observation can be performed in the same equipment as that employed for observation.

This application relates to subject matter disclosed in Japanese Application number 5-300322, filed on Nov. 30, 1993, the disclosure of which is incorporated herein by reference.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A method for preparing a sample for observation, the sample having a surface, said method comprising:

delivering a spray of an organic compound vapor to a first area of the sample surface while scanning the first area with a focussed ion beam to decompose the organic compound into a layer having a mask function, wherein the layer covers the first area and at least part of the first area has a width; and delivering a spray of an etching gas to a second area of the sample surface while irradiating the second area with an ion beam in order to remove material from the sample surface at the second area, thereby leaving an isolated portion of the sample, wherein the second area includes at least part of the first area, the layer covering the first area prevents removal of material from the sample surface in the first area and the isolated portion has a thickness equal to the width of the part of the first area.

2. A method as defined in claim 1 wherein the sample is an integrated circuit semiconductor.

3. A method as defined in claim 1 wherein in the etching gas is a halogen gas or a halogen compound gas.

4. A method as defined in claim 1 wherein the organic compound vapor is a hydrocarbon gas or a metal carbonyl vapor.

5. A method as defined in claim 1 comprising the preliminary steps of: observing the sample surface by irradiating the sample surface with a focussed ion beam and detecting secondary charged particles emitted from the sample surface; and identifying at least one of the areas based on the result of said observing step.

6. A method as defined in claim 5 wherein: said step of delivering a spray to a second area results in creation of a projecting portion of the sample, which projecting portion underlies the first area and has an observation surface perpendicular to the sample surface; and said method further comprises, after said step of delivering a spray to a second area, observing the observation surface.

7. A method as defined in claim 6 wherein said steps of observing the sample and observing the observation surface are carried out with a transmission electron microscope.

8. A method as defined in claim 7 wherein said steps of observing the sample and observing the observation surface are carried out with the same transmission electron microscope.

9. A method as defined in claim 1 wherein the first area is rectangular.

10. A method as defined in claim 9 wherein the same ion beam is used in both of said delivering steps, the ion beam is focussed and each said irradiating step comprises scanning the respective area with the focussed ion beam.

11. A method as defined in claim 10 wherein each said delivering step comprises spraying respective areas from respective small diameter nozzles, wherein: said step of delivering a spray to a second area results in creation of a projecting portion of the sample, which projecting portion underlies the first area and has an observation surface perpendicular to the sample surface; and said method further comprises, after said step of delivering a spray to a second area, observing the observation surface.

12. A method as defined in claim 1 wherein: said step of delivering a spray to a second area results in creation of a projecting portion of the sample, which projecting portion underlies the first area and has an observation surface perpendicular to the sample surface; and said method further comprises, after said step of delivering a spray to a second area, observing the observation surface.

13. A method as defined in claim 1 wherein the first area has an end portion which extends beyond the second area.

14. A method as defined in claim 1 further comprising, after removal of material from the sample surface at the second area, performing TEM observation of a portion of the sample which has been exposed by that removal of material.

* * * * *